United States Patent
Edmonds

(10) Patent No.: US 6,622,309 B1
(45) Date of Patent: Sep. 23, 2003

(54) ATHLETIC FACE SHIELD

(76) Inventor: Joseph Edmonds, 4154 162nd St., Lawndale, CA (US) 90260

( * ) Notice: Subject to any disclaimer, the term of this patent is extended or adjusted under 35 U.S.C. 154(b) by 0 days.

(21) Appl. No.: 10/120,249

(22) Filed: Apr. 10, 2002

Related U.S. Application Data

(60) Provisional application No. 60/282,598, filed on Apr. 10, 2001.

(51) Int. Cl.[7] .......................... A41D 13/00; A61F 9/00; A63B 69/00
(52) U.S. Cl. ...................... 2/9; 2/15; 473/450
(58) Field of Search .................. 2/9, 15, 11, DIG. 11, 2/433; 473/450

(56) References Cited

U.S. PATENT DOCUMENTS

| | | | | |
|---|---|---|---|---|
| 1,807,475 A | * | 5/1931 | Gibson | 2/15 |
| D204,023 S | * | 3/1966 | Potts | 2/15 |
| 3,686,690 A | * | 8/1972 | Webb | 2/9 |
| 3,868,108 A | * | 2/1975 | Kirchner | 473/450 |
| 5,123,116 A | * | 6/1992 | Roth | 2/15 |
| 5,267,353 A | * | 12/1993 | Milligan | 2/9 |
| 5,673,431 A | * | 10/1997 | Batty | 2/9 |
| 6,141,797 A | * | 11/2000 | Buck | 2/15 |

* cited by examiner

*Primary Examiner*—Rodney M. Lindsey
(74) *Attorney, Agent, or Firm*—Roger A. Marrs

(57) ABSTRACT

The athletic face shield consists of a head frame that contours to a player's head along with an elastic headband. The interchangeable hand shield is affixed to the front of the head frame and can be replaced with other objects. The athletic face shield fits in front of the player's face to produce the "hand in your face" affect utilized by defense players. It allows a solitary player to practice his or her defense game and experience the defense hand in their face when shooting.

6 Claims, 1 Drawing Sheet

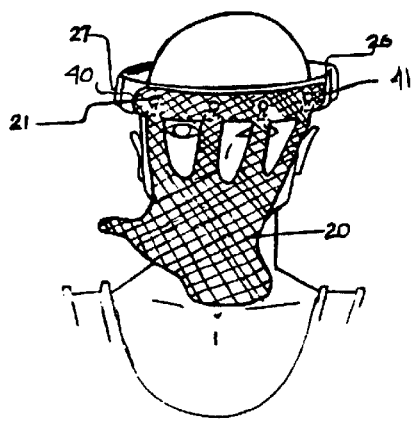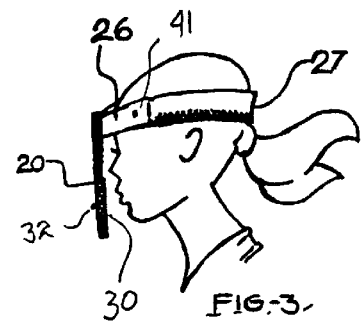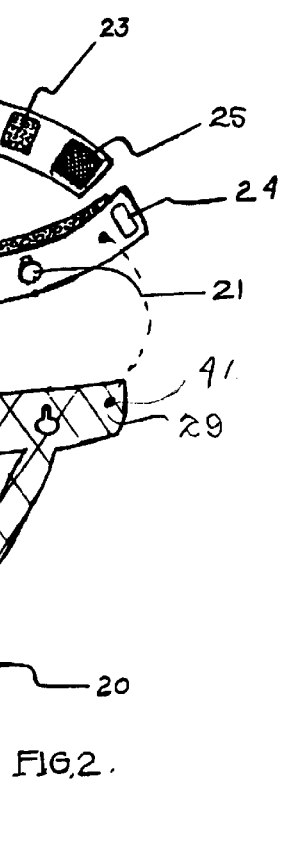

ATHLETIC FACE SHIELD

This application claims the benefit of Provisional Application Ser. No. 60/282,598 filed Apr. 10, 2001.

BACKGROUND OF THE INVENTION

1. Field of the Invention

The present invention relates to the field of face shield devices and more particularly to a novel face shield made in the shape of a hand. The hand is interchangeable and comes in various sizes to accommodate the user. The hand attaches to a headband-like frame that fits around a player's head. The hand is designed to substantially block his or her view while shooting a basketball.

2. Brief Description of the Prior Art

In the past, during basketball practice, coaches placed brooms, mops and other foreign objects in front of a basketball player's face in an attempt to mimic the "hand in your face" defense maneuver used by defense players. The reason for obstructing a player's view during practice sessions was to develop and increase the player's level of defense skills. Even though brooms, mops, and other objects were used to obstruct a player's view, these inappropriate items did not warrant the safety of the player, nor did they necessarily increase a player's skill level. Not only can these awkward objects hurt a player, they also do not imitate the real-life "hand in your face" maneuver.

Therefore, there has been a substantial need by athletic players and coaches in defense-related sports to utilize a device that replicates the "hand in your face" maneuver. The present invention provides a contoured headband frame where the interchangeable hand shield is affixed. The headband frame contours to the player's head along with an adjustable elastic-like band. The hand shield attaches to the frame and is designed to fit in front of the player's face to produce the real-life "hand in your face" affect. The interchangeable hand shield in front of the frame can be removed so that other hand configurations and sizes can be attached to the frame in order to accommodate the user. The interchangeable feature of this novel face shield also allows the user to replace the interchangeable hand shield with an optional sun-shield attachment that protects them from harmful UV-Rays off the court.

SUMMARY OF THE INVENTION

Accordingly, the above problems and difficulties are avoided by the present invention which provides a new method of athletic training through the use of a novel face shield. The athletic face shield consists of a head frame that contours to a player's head along with an elastic headband. The interchangeable hand shield is affixed to the front of the head frame, and can be replaced with other objects. The athletic face shield is designed to fit in front of the player's face to produce the "hand in your face" affect utilized by defense players. Its unique design allows a solitary player to practice his or her defense game and experience the defense "hand in the face" when shooting.

Therefore, it is among the primary objects of the present invention to provide a safe and convenient training tool for athletes, such as basketball players. The shield offers athletes a more natural means of view obstruction during practice. In addition, the hand size and configuration of the face shield can be changed to accommodate the user (child or adult). Also, UV sun shields can be attached to the head frame to protect users from harmful rays off the court Another object of the present invention is to provide a versatile and novel training tool for the purpose of improving a player's peripheral alertness as well as their shooting skills no matter what their present level of skill is.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood with reference to the following description, taken in connection with the accompanying drawings in which:

FIG. 1 is a front perspective view illustrating an athlete wearing the face shield of the present invention. The illustration demonstrates the face shield being utilized as a practice tool by a basketball player. The face shield is mimicking the "hand in your face" defense technique.

FIG. 2 is a front layout drawing of the face shield disassembled. The hand shield is interchangeable with the head frame. The head frame backing is cushioned to ensure user comfort. Each end of the elastic headband is looped through the holes located on both sides of the head frame, and then attached/secured by Velcro means.

FIG. 3 is a side view drawing of FIG. 1, which illustrates how the novel face shield attaches to the head. This side illustration also indicates that there is some distance between the face shield and the user. The hand itself is suspended by the head frame and securely fitted by the elastic headband.

DESCRIPTION OF PREFERRED EMBODIMENT

The present invention is illustrated in FIGS. 1–3 inclusive which provides an athletic training device using a novel face shield 20. The athletic face shield consists of a head frame 24 that contours to a player's head along with an elastic headband 27. The interchangeable face shield is affixed to a front 26 of the head frame by stud 21 and aligned slots 19 and can be replaced with other objects. The athletic face shield is designed to fit in front of the player's face to produce the "hand in your face" affect utilized by defense players. It allows a solitary player to practice his or her defense game and experience the defense hand in their face when shooting. A two component fastener 23 and 25 secures the head frame 21 together when end carrying component 25 is inserted through slot 24 and joined with component 23.

Therefore, the present invention provides a safe and convenient training tool for athletes, such as basketball players. The shield offers athletes a more natural means of view obstruction during practice. In addition, the space between the fingers of the face shield can be changed to accommodate the user. A false hand 30 having fingers, such as finger 31, can be rotated about a pivot 32 to open or close the viewing ports or space between shield fingers such as defined between fingers 33 and 34.

The shield includes a front section 29 having opposite ends that are pivotally secured to the head frame at the ends of the front section 26 as indicated by numerals 40 and 41.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. An athletic face shield comprising:

a head frame;

a face shield detachably carried on said head frame and downwardly depending therefrom;

said face shield having a plurality of openings permitting limited viewing therethrough by the user;

said head frame includes a front section and an elastic portion joined together by a two component fastener; and said face shield having an attachment portion corresponding to said front section and detachably coupled thereto by alignment of studs and notches respectively disposed on said front section and said attachment portion, the aligned studs and notches enabling the attachment portion to follow the curve of a wearer's forehead when the athletic face shield is worn.

2. The shield defined in claim 1 wherein:

said face shield includes a multiplicity; of elongated sight blocking fingers connecting said attachment portion to a hand portion and said plurality of openings defined between adjacent ones of said fingers.

3. The shield defined in claim 2 including:

a false hand portion pivotally connected to said hand portion and having spaced-apart fingers adapted to open and partially close said plurality of openings upon rotation of said false hand portion via said pivotal connection.

4. The shield defined in claim 3 including:

a cushion member attached to said front section bearing against the head of the user.

5. The shield defined in claim 4 wherein:

said attachment portion is pivotally carried on said head frame and rotatably adapted to raise said face shield when said attachment studs and notches are not coupled.

6. An athletic face shield comprising:

a head frame;

a face shield detachably carried on said head frame and downwardly depending therefrom;

said face shield having a plurality of openings permitting limited viewing therethrough by the user; and a false hand member pivotally carried on said shield and having finger projections adapted to restrict viewing through said openings as said false hand member is pivoted on said shield.

* * * * *